United States Patent [19]

Fleischhacker, Jr.

[11] Patent Number: 5,433,200
[45] Date of Patent: Jul. 18, 1995

[54] LOW PROFILE, COATED, STEERABLE GUIDE WIRE

[75] Inventor: Joseph F. Fleischhacker, Jr., Mound, Minn.

[73] Assignee: Lake Region Manufacturing, Inc., Chaska, Minn.

[21] Appl. No.: 976,522

[22] Filed: Nov. 16, 1992

Related U.S. Application Data

[63] Continuation-in-part of Ser. No. 789,870, Nov. 12, 1991, abandoned, which is a continuation-in-part of Ser. No. 549,740, Jul. 9, 1990, Pat. No. 5,069,217.

[51] Int. Cl.[6] ............................................. A61B 6/00
[52] U.S. Cl. .................................. 128/657; 128/772; 604/170; 604/280; 604/282
[58] Field of Search ............... 128/772, 657; 604/9, 604/167, 170, 280, 282

[56] References Cited

U.S. PATENT DOCUMENTS

| | | | |
|---|---|---|---|
| 4,003,369 | 1/1977 | Heilman et al. | 128/772 |
| 4,724,846 | 2/1988 | Evans, III | 128/657 |
| 4,813,434 | 3/1989 | Buchbinder et al. | 128/657 |
| 4,846,186 | 7/1989 | Box et al. | 128/657 |
| 5,060,660 | 10/1991 | Gambale et al. | 128/772 |
| 5,065,769 | 11/1991 | de Toledo | 128/772 |
| 5,069,217 | 12/1991 | Fleischhacker, Jr. | 128/657 |
| 5,213,111 | 5/1993 | Cook et al. | 128/772 |
| 5,234,003 | 8/1993 | Hall | 128/772 |
| 5,243,996 | 9/1993 | Hall | 128/772 |
| 5,365,942 | 11/1994 | Shank | 128/772 |

Primary Examiner—William E. Kamm
Assistant Examiner—Robert L. Nasser, Jr.
Attorney, Agent, or Firm—Grady J. Frenchick

[57] ABSTRACT

A guide wire having a solid core wire which runs its entire length. The core wire has a proximal portion which constitutes the majority of its length and which tapers to a distal portion. The distal portion terminates in an atraumatic tip at the extreme distal end of the guide wire. In one embodiment a portion of the distal segment of the core wire adjacent the tip is flattened. The guide wire further includes an integral, flexible, flat wire coil attached to the core wire at its taper and to the core wire distal tip and running the entire distance therebetween. Lastly, the flattened wire coil has a nonmetallic lubricous or hydrophilic coating on at least a portion of its exterior. In a preferred embodiment the proximal portion of the core wire tapers to a second diameter medial portion or segment which itself tapers to a third diameter distal segment. In another embodiment, the coils of the flat wire coil are closely wound or touching through a majority of the length of the coil and are separated adjacent the guide wire tip.

8 Claims, 4 Drawing Sheets

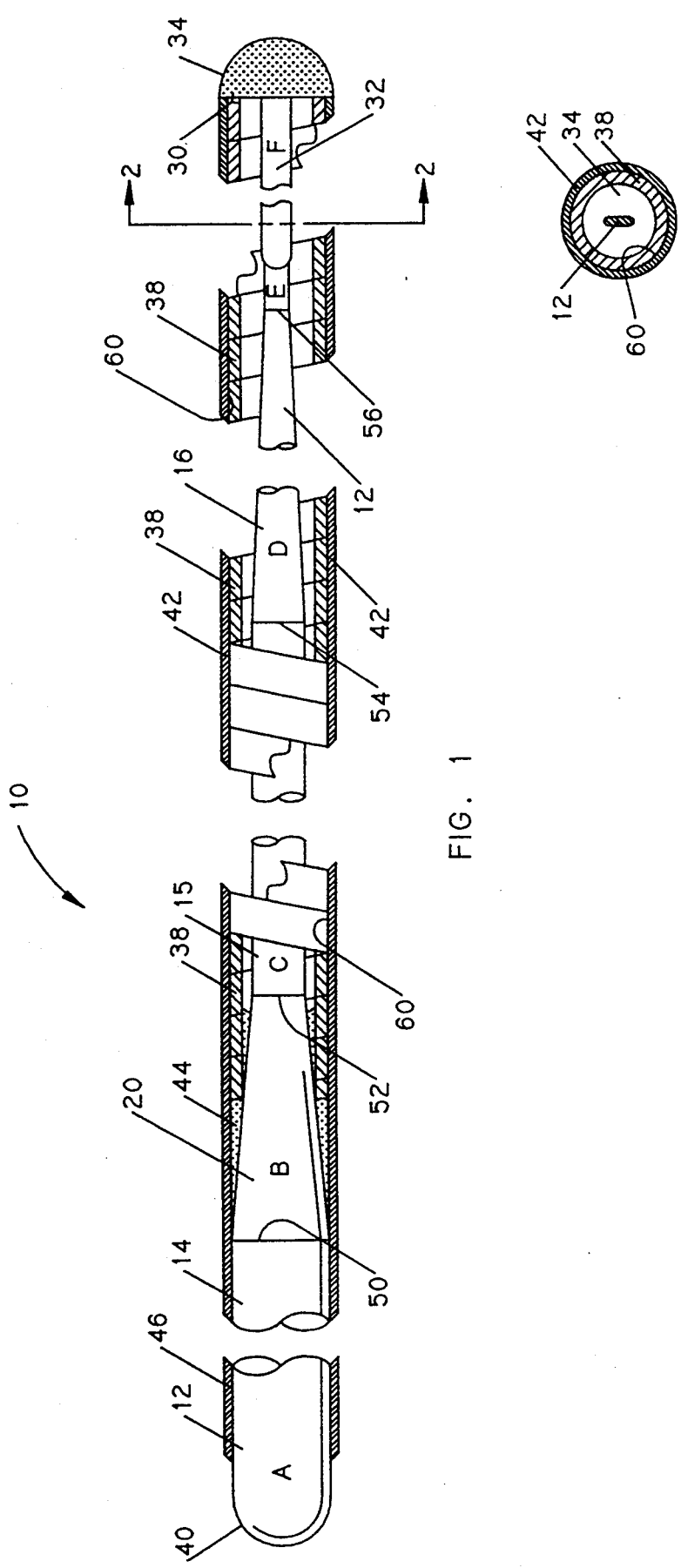

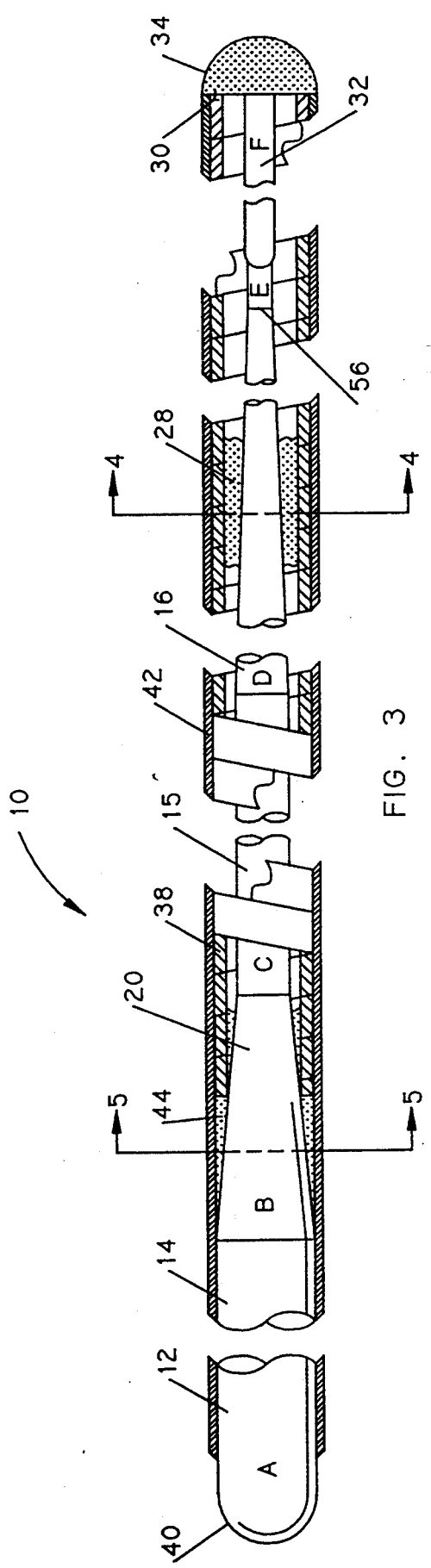

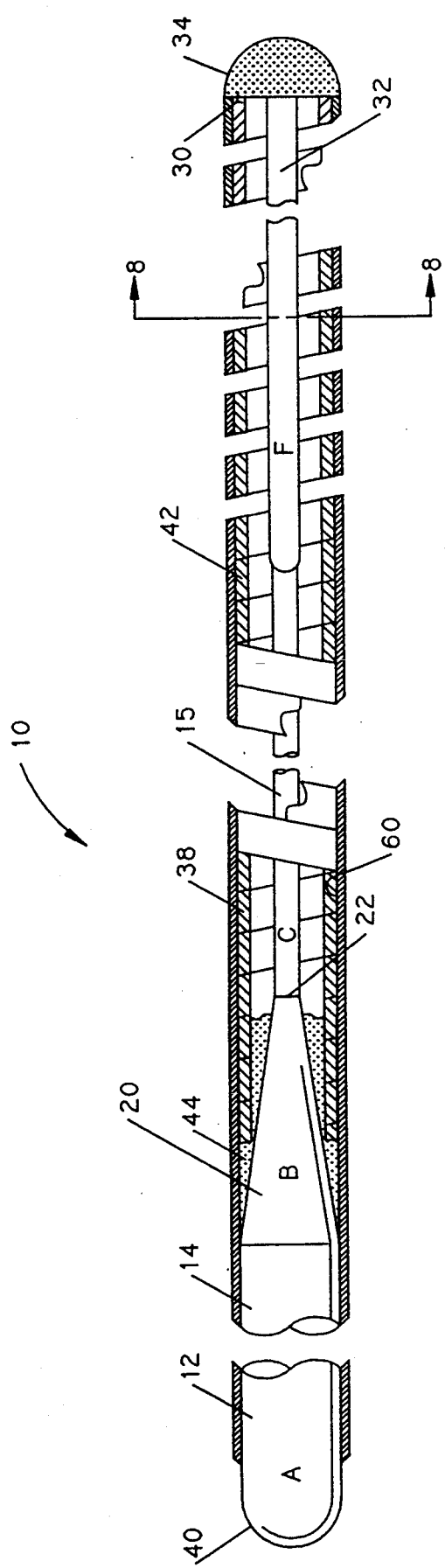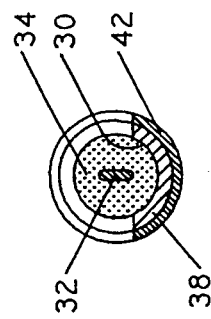

LOW PROFILE, COATED, STEERABLE GUIDE WIRE

CROSS REFERENCE TO CO-PENDING APPLICATIONS

This application is a continuation-in-part of a patent application Ser. No. 07/789,870 filed Nov. 12, 1991 now abandoned, which was a continuation of Ser. No. 07/549,740 filed Jul. 9, 1990, now U.S. Pat. No. 5,069,217.

BACKGROUND OF THE INVENTION

1. Field of the Invention

The present invention relates generally to devices for use in medical procedures. More particularly, this invention relates to low profile, coated guide wires for directing a catheter or other medical device through the cardiovascular system or other passage way in the human body.

2. Description of the Prior Art

The use of guide wires for positioning medical devices within the vessels of a body has been known for some time. A common current application for guide wires is an antecedent step to a percutaneous translumenal coronary angioplasty (PTCA) procedure. In this step, a guide wire is maneuvered, steered, or directed from an entry point in the arterial system, such as the femoral artery, to the site of an occlusion for example, in a coronary artery. A dilatation catheter then is advanced over the guide wire to the treatment site where the PTCA procedure is performed.

In PTCA applications, it is necessary that the guide wire have a small diameter, be flexible enough to negotiate the tortuous arterial pathways without danger of perforation, and have sufficient steerability to permit the attending physician to select the desired pathway from a number of alternatives as branches in the arterial system are encountered. The ideal guide wire, therefor is steerable, has a flexible and bendable tip, and has the ability evenly to transmit torque or translational movement from its proximal end to its distal end.

U.S. Pat. No. 4,538,622 to Samson et al. discloses a guide wire comprising an elongate flexible cylindrical element, e.g., a core wire, the elongate cylindrical element being tapered at its distal end, the distal end having two wire coils disposed thereabout. The two wire coils abut each other at their respective distal and proximal ends. The two coils comprise different materials, the more distal of the two coils comprising a radiopaque material and terminating at its extreme distal end in an atraumatic tip. In some embodiments of the invention disclosed in the '622 patent, the flexible, cylindrical element terminates within the two coil structure short of the guide wire tip and is connected to the tip by means of a safety wire or safety ribbon.

U.S. Pat. No. 4,763,647 to Gambale, and U.S. Pat. No. 4,545,390 to Leary, are similar to the Samson '622 patent discussed above in that they disclose guide wires having core wires which terminate short of the extreme distal end of the coil into which the central core wire is inserted.

U.S. Pat. No. 4,808,706 to Heilman et al. discloses a method for manufacturing catheter guidewire. In one embodiment, the guidewire of the Heilman '706 patent is developed from a coiled semi-rectangular flatwire which has been coated with a surface lubricant such as Teflon prior to winding. The Heilman et al. '706 patent is a division of an application which produced related Heilman et al. U.S. Pat. No. 4,003,369.

U.S. Pat. No. 4,895,168 to Machek discloses a moveable core guidewire assembly comprising a wire wound cylindrical casing having a distal closed end and a proximal open end. Between the proximal and distal ends of the cylindrical casing is a resilient moveable core wire. The assembly further includes a plastic safety cover coextensive with and surrounding the wire wound cylindrical casing.

U.S. Pat. No. 4,724,846 to Evans, III discloses a catheter guide wire assembly that has a combined core and safety wire extending longitudinally between its proximal and distal ends. A wound wire is positioned around the combined core and safety wire and follows the countour thereof. The combined core and safety wire of the Evans, III '846 patent has proximal, intermediate, and distal segments with different diameters.

None of the above patents or other references alone or in combination, disclose or suggest the present invention.

SUMMARY OF THE INVENTION

Briefly, in one aspect, the present invention is a low profile, coated, flexible, steerable guide wire for use in a medical procedure, such as coronary angioplasty. "Low profile" as the term is used herein generally means small overall guide wire diameter, i.e., generally less than about 0.020 inches. The present invention overcomes the problems found in the prior art by providing a small diameter guide wire, which is flexible yet steerable, while providing greater safety and the desired trackability.

The solid core wire, in conjunction with the required configuration of the coil wire permits a larger overall diameter core wire to be used. This, in turn, provides an enhanced longitudinal stiffness which is sometimes necessary to improve catheter trackability over the guide wire. Further, if a thicker core wire is not needed to provide longitudinal rigidity or "stiffness" then a device with a lesser overall diameter can be used.

These and other advantageous features are obtained through the use a guide wire or guide wire assembly having of a solid core wire which extends the entire length of the guide wire. Near its distal end, the core wire has a taper from its main segment or first diameter portion to a second, lesser or smaller diameter distal portion. The smaller diameter, distal portion terminates in an atraumatic, smoothly rounded tip. Optionally, to enhance flexibility, part of the distal portion of the core wire adjacent the atraumatic tip may be flattened.

There is disposed about the second diameter, distal portion of the core wire a single, integral, single piece, flat wire coil. The proximal end of the flat wire coil is connected to the core wire body at about the region of the taper and the distal end of the coil is connected to the atraumatic tip.

Completing the structure, the flat wire coil has, on its outer or exposed surface, a coating of a lubricous, non-thrombogenic or abrasion resistant material, the coating preferably running the entire distance between the points where the flat wire coil is connected to the core wire body at its taper and its tip.

In a preferred practice of this invention, the core wire has a first taper from the main diameter or proximal portion of the core wire body to an intermediate, lesser diameter, medial portion. Closer to the core wire distal tip, the core wire has a second taper from the medial, second diameter portion to yet a smaller diameter distal portion. The distal portion of the core wire body terminates in an atraumatic rounded, or hemispherical, usually brazed, tip. Optionally, the distal portion of the core wire may be flattened immediately adjacent the tip to enhance guide wire flexibility. In another practice of this invention, the flat wire coil is coupled to the core wire at the first and second core wire tapers as well as the core wire distal tip. In yet a further practice of this invention, the individual helices of the flat wire coil are contiguous or touching over at least a substantial portion of the coil and are separated or spaced apart from each other over some remaining portion (usually the extreme distal portion) of the coil. Whether the one taper or the two taper embodiments of the invention are employed, a single, at least partially exteriorly coated, flat wire coil extends from the most proximal (usually first taper) to the tip and is coupled thereto at those two locations.

The proximal end of the guide wire is configured to correspond to the particular application. For PTCA use, the proximal end of the guide wire is of a diameter and configuration which permits insertion of the dilatation catheter after the guide wire has been properly positioned.

BRIEF DESCRIPTION OF THE DRAWINGS

Other objects of the present invention and many of its attendant advantages will be readily appreciated as the same become better understood by reference to the following detailed description of the invention when considered in connection with the accompanying drawings, in which like reference numerals designate are used to designate like features throughout the FIGURES and wherein:

FIG. 1 illustrates a partially sectioned plan view of a guide wire of the present invention;

FIG. 2 illustrates a cross-sectional view of the distal end of the guide wire taken along line 2—2 of FIG. 1;

FIG. 3 illustrates a second embodiment of the present invention;

FIGS. 4 and 5 are section views of the embodiment of the invention shown in FIG. 3 taken along lines 4—4 and 5—5, respectively;

FIG. 7 is yet a fourth embodiment of this invention;

FIG. 8 is a partial section view of the embodiment of the invention shown in FIG. 7 taken along line 8—8.

DETAILED DESCRIPTION OF THE INVENTION

Figure 6:
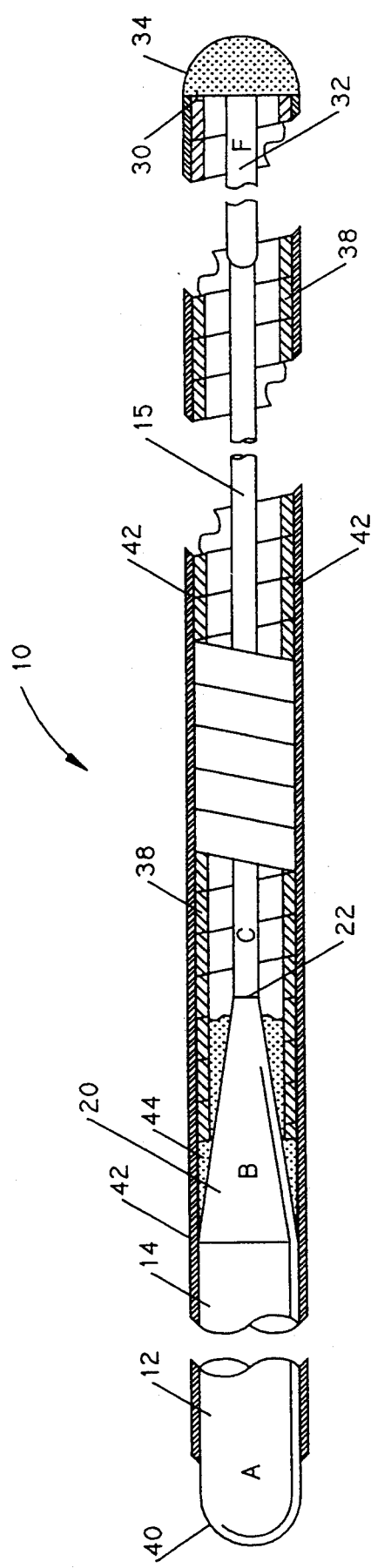
FIG. 6 is a further embodiment of the present invention.

FIG. 1 is a plan view of a preferred embodiment of a guide wire 10 of the present invention. The guide wire of FIG. 1 is shown in partial section better to illustrate the interior details of its construction and its operation. The inner element of guide wire 10 is a core wire 12. Core wire 12 extends the entire length of guide wire 10, terminating in hemispherical, atraumatic distal tip 34. For descriptive purposes, core wire 12 has been marked with letter designations A–F (and corresponding numerical designations). Core wire 12 comprises solid metal, preferably comprising 304 stainless steel or other similar metal or alloy suitable for acute use in the human body. By way of example and for purposes of illustration only, for PTCA applications, core wire 12 (and therefore guide wire 10) is approximately 180 cm. in length between from its proximal end to its atraumatic tip. For other applications, other lengths and other arrangements of segments and features within those segments are within the skill of a person having knowledge of this art.

Core wire 12, at its proximal end 40, is configured as is appropriate for the intended application. As shown, proximal end 40 is substantially hemispherical having a diameter in the range of about 0.012 to 0.020 inches. Core wire proximal end 40 can be configured for utilization with an extension system.

Turning to the details of the guide wire structure of FIG. 1, the main body, proximal segment A (14) of core wire 12 is approximately 150 cm. in length and has a constant first or main diameter in the range of about 0.012–0.020 inch. The main body segment A of core wire 12 has a first taper at segment B (20) to medial segment C. Taper B has a length of about 2 cm beginning at line 50 and terminating at line 52. As shown, medial or intermediate segment C (15) has a second, intermediate diameter which is substantially constant between segment B and second taper D, the proximal end of which is shown at line 54. Core wire 12 has a second taper at segment D (16) to distal segment E. Segment D tapers over a 4–15 cm. distance shown at lines 54 to 56. Distal segment E has third constant diameter segment. The distance between line 50 and tip 34 is about 30 cm.

Segment E of core wire 12 optionally is flattened (over the extreme distal 2 cm) adjacent distal tip 34 at segment F. The most distal 2 cm. of core wire 12 may be flattened at 32 to reduce guide wire stiffness and achieve greater flexibility in a direction normal to the plane of the flattened face of Segment F.

The guide wire of FIG. 1 further includes a flexible, flat wire coil 38. Flat wire coil 38 is radially disposed about the medial and distal segments of core wire 12 and extends over the entire distance. Flat wire coil 38 is coupled to and is in intimate contact with the core wire 12 at first taper 20 and tip 34 and preferably is brazed to the core wire at each of its ends at brazes 30 and 44. Flat wire coil is oblate or prolate in section having major and minor axes with ratios in the range of about 1.2:1 to 3:1. Flat wire coil 38 has an outside diameter in the range of about 0.010 to about 0.020 inch and an inside diameter in the range of about 0.008 to about 0.016 inch. At the distal end, flat wire coil spring 38 and core wire 12 are coextensive. These two components are fixedly attached by the hemispherical weld 34 which provides a smooth distal tip for insertion and maneuvering of the guide wire 10. Flat wire coil spring 38 may comprise a radiopaque material or a non-radiopaque material depending upon application.

Flat wire coil 38 includes, on at least a portion of its exterior 60, a coating 42. In a preferred practice, the coating 42 may impart a number of desired qualities to the guide wire. For example, coating 42 may be lubricous, hydrophilic, abrasion resistant or non-thrombogenic (or have a combination of these characteristics), depending upon design preference and guide wire application. U.S. Pat. No. 4,100,309, and 4,119,094 both to Michael J. Micklus et al., 4,624,267 to Walter S. Creasy et al. 5,001,009 to Richard J. Whitbourne, and 4,925,445 to Hidetoshi Sakamoto et al., the teachings of which are incorporated by reference herein, all disclose coatings which could be applied to at least a portion of the outer surface of flat wire coil 38. Other coatings which could be used include polytetrafluoroethylene (PTFE) and silicone.

Generally speaking the above coatings are applied using conventional application techniques such as spraying, or dip coating. Also generally speaking, the coatings are applied to a thickness needed to impart the desired characteristic to the guide wire. Coating thicknesses in the range about 0.0001 inches to about 0.002 inches are preferred.

The main body 14 of core wire 12 optionally may be coated with a polymer 46 to change its handling characteristics. Main body 14 may be completely coated or some portion may be left uncoated. In a preferred embodiment, this is a polymer coating of polytetrafluoroethylene (PTFE), silicone, or any other suitable coating of about 0.0005 inch. Main body coating or polymer 46 may have the same composition or a different composition from that of flat wire coating 42. Multiple coatings may be applied in layered or abutting arrangement. Preferably, the most proximal 2-3 cm. of proximal segment A is left uncoated as illustrated in the FIGURE.

FIG. 2 is a cross sectional view of the distal tip of core wire 12 as optionally flattened along length 32. Such flattening of core wire 12 provides increased flexibility. After flattening, core wire 12 along length 32 has cross sectional dimensions of about 0.004 inch by 0.002 inches providing a ratio in the range of 2:1.

The above-described flat wire coil construction, particularly in conjunction with the flattened distal segment, provides a unique combination of handling characteristics and tactile sensation to the user of the guide wire. The guide wire has extreme flexibility in at least some dimensions and is coupled with a very low profile. Moreover, the flat wire construction permits the distal segment of the device to be coated without significantly increasing the overall diameter or device profile beyond that of main diameter segment A and while maintaining a large coil lumen. This combination of features is believed to be unique.

FIG. 3 shows a second embodiment of the present invention. The primary difference between the embodiments of FIG. 3 and FIG. 1 is that in FIG. 3 flat wire coil 38 has been coupled, e.g., at braze 28, to core wire 12 at second taper 16. This coupling of the flat wire coil to core wire 12 intermediate the opposite ends of coil 38 increases the steerability and enhances the handling characteristics of the guide wire.

FIGS. 4 and 5 are transverse section views of the guide wire of FIG. 3 taken through the two brazes, 28 and 44, respectively where the coil is attached to the core wire at first and second tapers 20, 16. Braze material 62 is conventional and is well known in the guide wire art.

FIG. 6 is another embodiment of the invention in which the core wire has only a distal segment 14 and a proximal segment 15 joined by a single taper 20. The individual helices or coils of flat wire coil 38, in this embodiment, are touching throughout the length of the coil. All other details of the construction are as discussed above.

FIGS. 7 and 8 illustrate an embodiment of the invention in which the flat wire coil has a segment in which the individual coils are contiguous or touching and a second segment in which the individual coils are spaced apart. It is to be understood that spacing of the individual helices is a matter of design and application preference provided the flat wire coil is deployed throughout the structure. Spacing of the coils also imparts a different "feel" or handling characteristic to the guide wire. Generally speaking, the spaced coil configuration will have a greater tip flexibility. FIG. 8 shows a partial section view in which the space between the adjacent coils is clearly shown.

Figure 9:
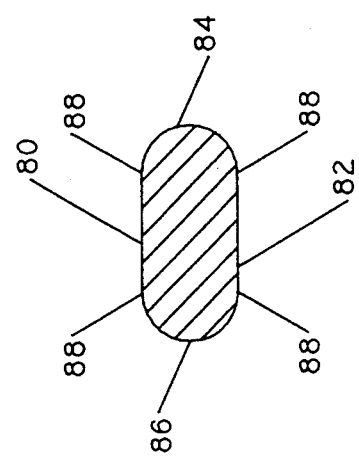
FIG. 9 is a cross sectional view of a preferred coil wire.

FIG. 9 illustrates a preferred form of a coil wire useable in the present invention in which the coil wire is oblate or prolate in section. An oblate coil wire has generally opposing or parallel flat, exterior and interior surfaces 80, 82, respectively, connected or coupled (at edges 88) by rounded or arcuate lateral surfaces 84, 86. Lateral surfaces 84, 86 may touch between adjacent coil helices or they may be spatially separated. An oblate coil wire presents many of the size and configurational advantages of a rectangular flat wire coil yet presents potentially less traumatic rounded edges 88 to a vessel in which a device is inserted. An oblate coil wire also permits individual coil helices to move more easilly with respect to each other. This may provide some ease of handling and tactility not obtainable with other guide wire structures.

Typical Guide Wire Dimensions

Using the above designations, approximate guide wire dimensions typically usaeable with the present invention are as follows:

| Section of the Core | Length, cm | Diameter, in. |
| --- | --- | --- |
| A-B | 150 | 0.012-0.020 |
| B-C | 2 | 0.016-0.010 |
| C-D | 5-15 | constant |
| D-E | 4-15 | 0.010-0.003 |
| E-F | 2 | flat cross section 0.002 -0.0045 |
| A-F | 180 | determined by above |
| B-F | 30 | determined by above |

The guide wire 10 of the present invention is utilized in medical procedures in accordance with generally accepted medical practices. Whether a guide wire of the present invention is used in a PTCA or other medical procedure its low profile, steerability and concomitant flexibility will be of great advantage.

Numerous characteristics and advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The invention's scope is, of course, defined in the language in which the appended claims are expressed.

What is claimed is as follows:

1. A guide wire comprising:
    a. a core wire including in order a proximal portion having a first diameter, said proximal portion having a distal end, the distal end including a taper, the taper coupling to a distal portion of the core wire, the distal portion terminating in a smooth distal tip;
    b. a flexible, flat wire coil attached to said taper, said flat wire coil having disposed on at least a portion of its exterior surface:
    c. a non-metallic coating material whereby said first diameter said core wire and said flexible flat wire coil provide for insertion, flexibility and maneuverability of said guide wire with flexibility and bendability of a distal end.

2. A guide wire according to claim 1 wherein at least part of a distal portion of the core wire adjacent the guide wire tip is flattened.

3. A guide wire according to claim 1 wherein the non-metallic coating comprises PTFE.

4. A guide wire assembly comprising;
   a. a core wire including in order a proximal portion having a first diameter, a first taper, a medial portion having a second diameter, a second taper, a distal portion, the distal portion having a third diameter and terminating in a smooth distal tip said guide wire further including:
   b. a flat wire coil attached to said core wire at said first tape, said flat wire coil having disposed on at least a portion of its exterior surface:
   c. a non-metallic coating material, whereby said third diameter of said core wire and said flexible wire coil provide for insertion, flexibility and maneuverability of said guide wire with flexibility and bendability of a distal end.

5. A guide wire assembly according to claim 4 wherein at least part of the distal portion of the core wire adjacent the tip is flattened.

6. A guide wire assembly according to claim 4 wherein the flattened coil wire is attached to said core wire at said second coil wire taper.

7. A guide wire assembly according to claim 4 wherein the non-metallic coating comprises a hydrophilic polymer.

8. A guide wire assembly according to claim 4 wherein the coating coats the entire exterior surface of the flat wire coil.

* * * * *